United States Patent [19]

Manning et al.

[11] Patent Number: 4,714,696
[45] Date of Patent: Dec. 22, 1987

[54] NOVEL DERIVATIVES OF ARGININE VASOPRESSIN ANTAGONISTS

[75] Inventors: Maurice Manning, Toledo, Ohio; Wilbur H. Sawyer, Scarsdale, N.Y.

[73] Assignees: Medical College of Ohio, Toledo, Ohio; Trustees of Columbia University, New York, N.Y.; a part interest

[21] Appl. No.: 574,257

[22] Filed: Jan. 26, 1984

[51] Int. Cl.⁴ .................... A61K 37/34; C07K 7/16
[52] U.S. Cl. .................................. 514/11; 530/315; 514/807
[58] Field of Search .............. 260/112.5 R; 514/11, 514/807; 530/315

[56] References Cited

U.S. PATENT DOCUMENTS

| | | | |
|---|---|---|---|
| 3,371,080 | 2/1968 | Boissonnas et al. | 530/315 |
| 3,415,805 | 12/1968 | Siedel et al. | 260/112.5 R |
| 3,418,307 | 12/1968 | Boissonnas et al. | 530/315 |
| 3,454,549 | 7/1969 | Boissonnas et al. | 530/315 |
| 3,497,491 | 2/1970 | Zooral et al. | 260/12.5 R |
| 3,691,147 | 9/1972 | Manning | 530/315 |
| 3,700,652 | 10/1972 | Manning | 530/315 |
| 3,752,799 | 8/1973 | Jost | 530/315 |
| 3,816,385 | 6/1974 | Gillessen et al. | 530/315 |
| 3,883,498 | 5/1975 | Gillessen et al. | 530/315 |
| 3,980,631 | 9/1976 | Prochazka et al. | 260/112.5 R |
| 4,081,533 | 3/1978 | Cheesman | 530/315 |
| 4,148,787 | 4/1979 | Mulder | 530/315 |
| 4,237,119 | 12/1980 | Cort et al. | 260/112.5 R |
| 4,285,858 | 8/1981 | Cort et al. | 260/112.5 R |
| 4,367,225 | 1/1983 | Manning et al. | 260/112.5 R |
| 4,399,125 | 8/1983 | Manning et al. | 530/315 |

OTHER PUBLICATIONS

Brtnik et al., 48, Collection Czechoslovak Chem. Commun., 2862 (1983).
Yim et al., 21, Int. J. Peptide Res., 568 (1983).
Dyckes et al., 17, J. Med. Chem., 250 (1974).
Manning et al., 20, J. Med. Chem., 1228 (1977).
Bankowski et al., 21, J. Med. Chem., 850 (1978).
Kruszynski et al., 23, J. Med. Chem., 364 (1980).
Lowbridge et al., 21, J. Med. Chem., 313 (1978).
Chan et al., 161, Science, 280 (1968).
Chan et al., 174, J. Pharmacol. Exp. Ther., 541 (1970).
Chan et al., 196, J. Pharmacol. Exp. Ther., 746 (1976).
Nestor et al., 18, J. Med. Chem., 1022 (1975).
Larsson et al., 21, J. Med. Chem., 352 (1978).
Sawyer et al., 212, Science, 49 (1981).
Manning et al., 24, J. Med. Chem., 701 (1981).
Merrifield, 85, J. Am. Chem. Soc., 2149 (1963).
Merrifield, 3, Biochemistry, 1385 (1964).
Manning, 90, J. Am. Chem. Soc., 1348 (1968).
Manning et al., 19, J. Med. Chem., 376 (1976).
Lowbridge et al., 20, J. Med. Chem., 1173 (1977).
Manning et al., 16, J. Med. Chem., 975 (1973).
Felix et al., 10, J. Peptide Protein Res., 299 (1977).
Botos et al., 22, J. Med. Chem., 926 (1979).
Hope et al., 237, J. Biol. Chem., 1563 (1962).
Schultz et al., 9, J. Med. Chem., 647 (1966).
Nestor et al., 18, J. Med. Chem., 284 (1975).
Huguenin et al., 39, Helv. Chem. Acta., 695 (1966).
Manning et al., 19, J. Med. Chem., 842 (1976).
Law et al., 82, J. Am. Chem. Soc., 4579 (1960).
Manning et al., Peptides, Structure, Function, Dan H. Rich and E. Gross, eds., Pierce Chemical Co., 257 (1981).
Manning et al., 25, J. Med. Chem., 45 (1982).
Butlen et al., 14, Mol. Pharmacol., 1006 (1978).
Sawyer et al., 5, Endocrinology, 40 (1974).
D. B. Case et al., 21, Progress in Cardiovascular Diseases, 195 (1978).
Bartter et al., 42, Am. J. Med., 790 (1967).
Gisin, 56, Helv. Chem. Acta., 1 1476 (1973).
Spackman et al., 30, Anal. Chem., 1190 (1958).
Konig et al., 103, Chem. Ber., 788 (1970).
Manning, 90, J. Am. Chem. Soc., 1348 (1968).
du Vigneaud, 76, J. Am. Chem. Soc., 3115 (1954).
Hope et al., 237, J. Biol. Chem., 1563 (1962).
Manning et al., 38, J. Chromatog., 396 (1968).
Moore, 238, J. Biol. Chem., 235 (1963).
Bodanszky et al., 81, J. Am. Chem. Soc., 5688 (1959).
Bodanszky et al., 39, J. Org. Chem., 444 (1974).
Dyckes et al., 17, J. Med. Chem., 969 (1974).
Schild et al., 2, Br. J. Pharmacol., 189 (1947).
Sawyer et al., 63, Endocrinology, 694 (1958).
Manning et al., 227, Nature, No. 5259, 715 (1970).
Baxter et al., 8, Biochemistry, 3592 (1962).

Primary Examiner—Delbert R. Phillips
Attorney, Agent, or Firm—Emch, Schaffer, Schaub & Porcello Co.

[57] ABSTRACT

Compounds acting as antagonists of the antidiuretic-/and or vasopressor activity of arginine vasopressin are those of the formula

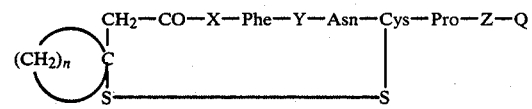

wherein n is 4 or 5; X is (D- or L-)Tyr(R), D-Phe, D-Val, D-Leu, D-Ile, D-Nva, D-Nle, D-Cha, D-Abu, D-Thr, D-Asn, D-Met or D-Gln; Y is Val, Ile, Thr, Ala, Lys, Cha, Nva, Met, Nle, Orn, Ser, Asn, Gln, Phe, Tyr, Gly, Abu or Leu; Z is (D- or L-) Arg, Orn or Lys; Q is Arg(NH₂), Ser(NH₂), (D- or L-)Ala(NH₂), Gly, OH or NH₂ and R is methyl, ethyl, propyl or butyl; provided that, when Y is Gln or Val, R may also be H.

28 Claims, No Drawings

NOVEL DERIVATIVES OF ARGININE VASOPRESSIN ANTAGONISTS

The invention described herein was made in the course of work under a grant or award from the Department of Health and Human Services.

BACKGROUND OF THE INVENTION

This invention relates to novel peptides which antagonize the antidiuretic and/or vasopressor action of arginine vasopressin in vivo.

PRIOR ART STATEMENT

Attempts to develop clinically useful synthetic antagonists of in vivo antidiuretic and/or vasopressor responses to arginine vasopressin, the antidiuretic hormone (ADH), have led to the synthesis and pharmacological evaluation of hundreds of analogs of the neurohypophysial peptides, oxytocin and vasopressin.

Analogs of vasopressin or oxytocin which antagonize antidiuretic responses to ADH have been reported by Chan et al., *Science*, vol. 161 (1968) at 280 and *J. Pharmacol. Exp. Ther.*, vol. 174 (1970) at 541 vol. 196 (1976) at 746; Dousa et al., *Science*, vol. 167 (1970) at 1134; Nestor et al., *J. Med. Chem.*, vol. 18 (1975) at 1022 and Larsson et al., *J. Med. Chem.*, vol. 21 (1978) at 352, herein incorporated by reference. None of the compounds reported has been pharmacologically or clinically useful as an antidiuretic antagonist.

The synthesis and evaluation of vasopressin analogs, incorporating etherified tyrosine at the 2-position, valine at the 4-position and D- or L-arginine at the 8-position, which antagonize the antidiuretic action of ADH in vivo, have been reported by Sawyer et al., *Science*, vol. 212 (1981) at 49; Manning et al., *J. Med. Chem.*, vol. 24 (1981) at 701; and Manning et al., U.S. Pat. Nos. 4,367,225 and 4,399,125, herein incorporated by reference.

Design of tissue-specific agonists and antagonists in the field of neurohypophysial peptides has been considered by Sawyer et al., *Molecular and Cellular Endocrinology*, vol. 22 (1981), 117-134; Manning et al., *The Pituitary*, Beardwell et al., eds., Butterworths, Kent, England (1981), 265-296; Manning et al., "Peptides, Synthesis, Structure, Function," Rich et al., eds., Pierce Chemical Co., (1981) at 257-260 and Manning et al., *J. Med. Chem.*, vol. 25 (1982) at 45 and 414.

Modification of oxytocin, containing a D-amino acid at the 2-position has been disclosed by Lebl et al., *Peptides*, Walter de Gruyter & Co., Berlin (1983), at 457. Other modifications, having a penicillamine unit at the 1- and 6-positions of vasopressin, have been disclosed by Simek et al., ibid, at 461. Modification of vasopressin analogs at the 9-position, for example, 1-deamino[9-D-alananimide]-AVP, has been investigated by Gazis et al., ibid., at 465.

It is therefore apparent that the correlation between structure of neurohypophysial peptides and action in vivo is not well understood and there is a continuing need for the development of pharmacologically and clinically effective antagonists of the antidiuretic action of arginine vasopressin.

OBJECT OF THE INVENTION

It is the object of the invention to provide novel antagonists of the antidiuretic and/or vasopressor action of ADH, which are effective in vivo.

SUMMARY OF THE INVENTION

This invention relates to novel antagonists of the antidiuretic and/or vasopressor action of ADH, which are compounds of the Formula I:

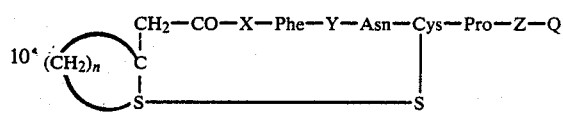

wherein X is (D- or L-)Tyr(R), D-Phe, D-Val, D-Ile, D-Nva, D-Nle, D-Cha, D-Abu, D-Thr, D-Asn, D-Gln or D-Met; Y is Val, Ile, Thr, Ala, Lys, Cha, Nva, Met, Nle, Orn, Ser, Asn, Gln, Phe, Tyr, Gly, Abu, or Leu; Z is (D- or L-)Arg, Orn or Lys; Q is $Arg(NH_2)$, $Ser(NH_2)$, (D- or L-)$Ala(NH_2)$, Gly, OH or $NH_2$ and R is methyl, ethyl, propyl or butyl; provided that when Y is Gln or Val, R may also be H.

This invention further relates to a method for antagonizing the in vivo antidiuretic and/or vasopressor response to ADH, comprising administering to an animal being treated an amount of a compound of Formula I, in admixture with a physiologically and pharmaceutically acceptable carrier, effective to antagonize the antidiuretic and/or vasopressor response to ADH.

DETAILED DESCRIPTION

Compounds of the invention, or comparison compounds of the prior art, are derivatives of arginine vasopressin. Amino acids are in the L-form, unless otherwise indicated. Each symbol, except for that of the 9-terminal substituent, is for the acyl (—C=O—) residue of the designated amino acid. For example, 9-OH represents a compound with a completed —COOH group of the amino acid residue at the 8-position and is, therefore, a desglycinamide compound. The correlation between full names and abbreviations is:

AVP, arginine vasopressin;
AVP-acid, deamido-arginine vasopressin, alternatively, vasopressinoic acid;
desGly[9]-AVP, desglycine-[9]-arginine vasopressin;
desGly($NH_2$)[9]AVP, desglycinamide[9]-arginine vasopressin;
d($CH_2$)$_5$AVP, [1-($\beta$-mercapto-$\beta$,$\beta$-cyclopentamethylenepropionic acid)]arginine vasopressin;
d($CH_2$)$_5$VDAVP, [1-($\beta$-mercapto-$\beta$,$\beta$-cyclopentamethylenepropionic acid), 4-valine, 8-D-arginine]-vasopressin;
d($CH_2$)$_5$Tyr(Me)VDAVP, [1-($\beta$-mercapto-$\beta$,$\beta$-cyclopentamethylenepropionic acid), 2-O-methyltyrosine, 4-valine, 8-D-arginine]vasopressin;
d($CH_2$)$_5$-D-TyrVDAVP, [1-($\beta$-mercapto-$\beta$,$\beta$-cyclopentamethylenepropionic acid), 2-D-tyrosine, 4-valine, 8-D-arginine]vasopressin;
d($CH_2$)$_5$-D-TyrVAVP, [1-($\beta$-mercapto-$\beta$,$\beta$-cyclopentamethylenepropionic acid), 2-D-tyrosine, 4-valine]-arginine vasopressin;
d($CH_2$)$_5$-Tyr(Me)AVP, [1-($\beta$-mercapto-$\beta$,$\beta$-cyclopentamethylenepropionic acid), 2-O-methyltyrosine]-arginine vasopressin;
desGly[9]d($CH_2$)$_5$AVP, [1-($\beta$-mercapto-$\beta$,$\beta$-cyclopentamethylenepropionic acid), 9-desglycine]-arginine vasopressin;

desGly(NH$_2$)$^9$d(CH$_2$)$_5$AVP, [1-($\beta$-mercapto-$\beta$,$\beta$-cyclopentamethylenepropionic acid), 9-desglycinamide]-arginine vasopressin;

d(CH$_2$)$_5$[D-Phe$^2$]VAVP, [1-($\beta$-mercapto-$\beta$,$\beta$-cyclopentamethylenepropionic acid), 2-D-phenylalanine, 4-valine]-arginine vasopressin;

desGly$^9$d(CH$_2$)$_5$[D-Phe$^2$]VAVP, [1-($\beta$-mercapto-$\beta$,$\beta$-cyclopentamethylenepropionic acid), 2-D-phenylalanine, 4-valine, 9-desglycine]-arginine vasopressin;

desGly(NH$_2$)$^9$d(CH$_2$)$_5$[D-Phe$^2$]VAVP, [1-($\beta$-mercapto-$\beta$,$\beta$-cyclopentamethylenepropionic acid), 2-D-phenylalanine, 4-valine, 9-desglycinamide]-arginine vasopressin;

d(CH$_2$)$_5$[D-Phe$^2$, Ile$^4$]AVP, [1-($\beta$-mercapto-$\beta$,$\beta$-cyclopentamethylenepropionic acid), 2-D-phenylalanine, 4-isoleucine]-arginine vasopressin;

desGly$^9$d(CH$_2$)$_5$[D-Phe$^2$, Ile$^4$]AVP, [1-($\beta$-mercapto-$\beta$,$\beta$-cyclopentamethylenepropionic acid), 2-D-phenylalanine, 4-isoleucine, 9-desglycine]-arginine vasopressin;

d(CH$_2$)$_5$[D-Tyr(Et)$^2$]VAVP, [1-($\beta$-mercapto-$\beta$,$\beta$-cyclopentamethylenepropionic acid), 2-D-(O-ethyl)-tyrosine, 4-valine]-arginine vasopressin;

desGly$^9$d(CH$_2$)$_5$[D-Tyr(Et)$^2$]VAVP, [1-($\beta$-mercapto-$\beta$,$\beta$-cyclopentamethylenepropionic acid), 2-D-(O-ethyl)tyrosine, 4-valine, 9-desglycine]-arginine vasopressin;

d(CH$_2$)$_5$[D-Phe$^2$, Ile$^4$, Arg-NH$_2$$^9$]AVP, [1-($\beta$-mercapto-$\beta$,$\beta$-cyclopentamethylenepropionic acid), 2-D-phenylalanine, 4-isoleucine, 9-argininamide]-arginine vasopressin;

d(CH$_2$)$_5$[D-Phe$^2$, Ile$^4$, Ser-NH$_2$$^9$]AVP, [1-($\beta$-mercapto-$\beta$,$\beta$-cyclopentamethylenepropionic acid), 2-D-phenylalanine, 4-isoleucine, 9-serinamide]-arginine vasopressin;

d(CH$_2$)$_5$[D-Phe$^2$, Ile$^4$, Ala-NH$_2$$^9$]AVP, [1-($\beta$-mercapto-$\beta$,$\beta$-cyclopentamethylenepropionic acid), 2-D-phenylalanine, 4-isoluecine, 9-alaninamide]-arginine vasopressin;

d(CH$_2$)$_5$[D-Phe$^2$, Ile$^4$, D-Ala-NH$_2$$^9$]AVP, [1-($\beta$-mercapto-$\beta$,$\beta$-cyclopentamethylenepropionic acid), 2-D-phenylalanine, 4-isoleucine, B 9-D-alaninamide]-arginine vasopressin;

desGly$^9$d(CH$_2$)$_5$[D-Phe$^2$, Ile$^4$]AVP, [1-($\beta$-mercapto-$\beta$,$\beta$-cyclopentamethylenepropionic acid), 2-D-phenylalanine, 4-isoleucine, 9-desglycine]-arginine vasopressin;

d(CH$_2$)$_5$[Tyr(Et)$^2$]VAVP, [1-($\beta$-mercapto-$\beta$,$\beta$-cyclopentamethylenepropionic acid), 2-(O-ethyl)-tyrosine, 4-valine]-arginine vasopressin desGly$^9$d(CH$_2$)$_5$[Tyr(Et)$^2$]VAVP, [1-($\beta$-mercapto-$\beta$,$\beta$-cyclopentamethylenepropionic acid), 2-(O-ethyl)-tyrosine, 4-valine, 9-desglycine]-arginine vasopressin and d(CH$_2$)$_5$[D-Phe$^2$, Ile$^4$]AVP acid, [1-($\beta$-mercapto-$\beta$,$\beta$-cyclopentamethylenepropionic acid), 2-D-phenylalanine, 4-isoleucine, 9-desamido]-arginine vasopressin.

The active peptides were synthesized by solid phase synthesis, as described by Bankowski et al. (1978), infra; Merrifield, *J. Am. Chem. Soc.*, vol. 85 (1963) at 2149 and *Biochemistry*, vol. 3 (1964) at 1385; Manning, *J. Am. Chem. Soc.*, vol. 90 (1968) at 1348; Manning et al., *J. Med. Chem.*, vol. 19 (1976) at 376; Lowbridge et al., *J. Med. Chem.*, vol. 20 (1977) at 1173; Manning et al., *J. Med. Chem.*, vol. 16 (1973) at 975; Kruszynski et al. (1980), infra; Sawyer et al., (1981), supra or Manning et al. (1981), supra.

Compounds of the 9-desglycine group, that is, Q is NH$_2$, are prepared as for other arginine vasopressin derivatives, except that one less cycle of deprotection, neutralization and coupling is employed. That is, the first amino acid residue, attached to resin, will be (D- or L-)Arg, rather than Gly, as would be the case for compounds in which Q is to be GlyNH$_2$.

Compounds in which the amino acid at the 9-position is other than Gly(NH$_2$) are prepared in a similar fashion, but by attaching an amino acid other than glycine to the resin at the start of the synthesis.

Desglycinamide compounds, that is Q is OH, in accordance with this invention are prepared as described in the examples.

The discovery of the antidiuretic antagonists d(CH$_2$)$_5$Tyr(alk)VAVP, Sawyer et al. (1981), supra, and Manning et al. (1981), supra, led to the synthesis of various analogs having a cyclopentamethylene ring structure and various substituents at the 2-position. Other modifications at the 4-, 6-, 7- and 8-positions, have been proposed.

It will also be understood that, when alkyl substituents (R) can be linear or branched, contemplated equivalents include all possible isomers.

Compounds of this invention, having an action antagonistic toward the antidiuretic action of arginine vasopressin are generally those wherein the 2-substituent is an amino acid of the D-series and the 4-substituent is an aliphatic amino acid. When the 4-substituent is Gln and the 2-substituent is of the L-series, it has been found that the compounds generally have specific antivasopressor action.

Most of compounds of Formula I are accordingly very effective antagonists of the antidiuretic response to ADH. They can therefore be used in pharmacological studies on the contribution of ADH to a variety of pathological states involving water retention. It is further contemplated that they could be effective and specific agents for treating the syndrome of inappropriate secretion of ADH, that is, the Schwartz-Bartter syndrome or SIADH. This syndrome can complicate a number of disorders, including carcinomas, pulmonary diseases, intracranial diseases and head injuries, Bartter et. al., *Am. J. Med.*, vol. 42 (1967) at 790. In addition, compounds of Formula I are effective as antagonists of the vasopressor response to ADH.

Compounds of Formula I, wherein X is Tyr and Y is Gln or X is Tyr(R), Y is Gln and R is H, methyl, ethyl, propyl or butyl, can be used in a similar fashion for conditions in which antivasopressor activity is indicated.

Surprisingly, activity of the compounds of the invention as antagonists of ADH or vasopressin is not lost by removal or modification of the 9-substituent. It is known that the chemical bond between the 8- and 9-positions is at least one point at which digestive enzymes, such as trypsin, attack vasopressin-type hormones. Therefore, compounds of this invention, if not themselves entirely stable toward digestive enzymes, will be useful in suggesting routes to peptide derivatives which will retain their activity when administered orally.

Retention of activity following hydrolysis of the C-terminal glycinamide of arginine vasopressin compounds, in accordance with this invention, is highly unexpected, in view of tryptic digestion of AVP to give desglycinamide$^9$-AVP, which had neither the antidiuretic nor the vasopressor activity, characteristic of AVP. See, du Vigneaud et al., *J. Am. Chem. Soc.*, vol. 75 (1953) at 4880.

The compounds of this invention can be employed in mixtures with conventional excipients, i.e., physiologically and pharmaceutically acceptable organic or inorganic carriers suitable for parenteral or other application, provided that the carriers do not interact deleteriously with the active compounds.

Suitable pharmaceutically acceptable carriers include, but are not limited to, water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethyl cellulose, polyvinyl pyrrolidone, etc. The pharmaceutical preparations can be sterilized and, if desired, mixed with auxiliary agents, e.g., lubricants, preservatives, stabilizers, wetting agents, emulsifiers, salts for influencing the osmotic pressure, buffers, coloring, flavoring and/or aromatic substances, which do not deleteriously interact with the active compounds.

For parenteral or intranasal application, solutions, preferably aqueous solutions, as well as suspensions, emulsions or implants, including suppositories, are particularly suitable. Ampoules are convenient unit dosages.

For enteral application, particularly suitable are tablets, dragees, or capsules, having talc and/or a carbohydrate carrier or binder or the like, the carrier preferably being lactose and/or corn starch and/or potato starch. A syrup, elixir or the like can be used, wherein a sweetened vehicle is employed. Sustained release compositions can be formulated, including those wherein the active compound is protected with differentially degradable coatings, e.g., by microencapsulation, multiple coatings, etc.

The compounds of Formula I are generally administered to animals, including but not limited to mammals, e.g, livestock, household pets, humans, cattle, cats and dogs. A diuretically effective daily dosage of the active compounds can be administered parenterally in a single dosage or as divided dosages throughout the day.

Parenteral or intranasal administration is preferred. The compounds of this invention are particularly valuable in the treatment of humans afflicted with water retention of any etiology. In this regard, they can be administered in substantially the same manner as the known compounds oxytocin and vasopressin, to achieve their physiological effects.

It will be appreciated that the actual preferred amounts of active compounds used will vary according to the specific compound being utilized, the particular compositions formulated, the mode of application, and the particular organisms being treated. Optimal application rates under/in a given set of conditions can be ascertained by those skilled in the art of using conventional dosage determination tests in view of the above guidelines.

DESCRIPTION OF PREFERRED EMBODIMENT

Preferred antidiuretic antagonists of Formula I are those wherein:
(a) X is D-Phe;
(b) X is D-Tyr(R) and R is methyl, ethyl, propyl or butyl;
(c) Y is Val, including each of (a)-(b);
(d) Y is Ile, including each of (a)-(b);
(e) Z is Arg, including each of (a)-(d);
(f) Q is $NH_2$, including each of (a)-(e);
(f) Q is $Arg(NH_2)$, including each of (a)-(e);
(h) Q is $Ser(NH_2)$, including each of (a)-(e);
(i) Q is (D- or L-)$Ala(NH_2)$, including each of (a)-(e)
(j) n is 5, including each of (a)-(i).

Most preferred compounds are those wherein n is 5, X is D-Phe, Y is Ile, Z is Arg and Q is $NH_2$ or $Ala(NH_2)$.

Preferred compounds are those in which Y is Gln are those wherein Z is Arg.

Without further elaboration, it it believed that one skilled in the art can, using the preceding description, utilize the present invention to its fullest extent. The following specific embodiments are, therefore, to be construed as merely illustrative and not limitative of the remainder of the disclosure in any way whatsoever. In the following Examples, the temperatures are set forth uncorrected in degrees Celsius. Unless otherwise indicated, all parts and percentages are by weight.

Chloromethylated resin (Bio-Rad Bio-Beads SX-1) was esterified by the procedure of Gisin, *Helv. Chim. Acta.*, vol. 56 (1973) at 1476 with Boc-Gly until 0.47 mmol./g. and $\sim 0.64$ mmol/g were incorporated. Amino acid derivatives, including Boc-Tyr(Me) ($R_f(A)$ 0.7, $R_f(B)$ 0.8) were supplied by Bachem or synthesized.

Triethylamine (TEA) and N-methylmorpholine (NMM) are distilled from ninhydrin.

Acetic acid used as the HCl-acetic acid cleavage reagent was heated under reflux with boron triacetate and distilled from the reagent. Dimethylformamide (DMF) was distilled under reduced pressure immediately before use. Methanol was dried with magnesium methoxide and distilled. Other solvents and reagents were analytical grade.

Thin layer chromatography (TLC) was done on silica gel plates (0.25 mm, Brinkmann Silplate) using the following solvent systems: A. cyclohexane-chloroform-acetic acid (2:8:1 v/v); B. propan-1-ol-ammonia (34%) (2:1 v/v); C. ethanol (95%)-ammonia (34%) (3:1 v/v); D. chloroform-methanol (7:3 v/v); E. butan-1ol-acetic acid-water (4:1:5 v/v, upper phase); F. butan-1-ol-acetic acid-water-pyridine (15:3:3:10 v/v). The applied loadings were 10–50 μg. The minimum length of the chromatograms was 10 cm. Chloroplatinate reagent and iodine vapor were used for development of the chromatograms.

Amino acid analysis of the peptides was done by the method of Spackman et al., *Anal. Chem.*, vol. 30 (1958) at 1190, in which peptide samples weighing about 0.5 mg were hydrolyzed with constant boiling hydrochloric acid (400 μl) in evacuated and sealed ampuoles for 18 h at 120° C. The analyses were performed using a Beckman Automatic Amino Acid Analyzer, Model 121. Molar ratios were referred to Gly=1.00. Elemental analyses were performed by Galbraith Laboratories, Inc., Knoxville, Tenn. The analytical results for the elements indicated by their respective symbols were within ±0.4% of theoretical values. Optical rotations were measured with a Bellingham Stanley, Ltd., Model A polarimeter, type pl.

EXAMPLE 1

β-(S-Benzylmercapto)-β,β-cyclopentamethylenepropionyl-Tyr(Me)-Phe-Gln-Asn-Cys(Bzl)-Pro-Arg(Tos)-Gly-NH$_2$

A. Combination of Solid Phase and Solution Methods

Boc-Tyr(Me)-Phe-Gln-Asn-Cys(Bzl)-Pro-Arg(Tos)-Gly-NH$_2$, prepared by the method of Bankowski et al., *J. Med. Chem.*, vol. 21 (1978) at 850 (319 mg, 0.26 mmol), was dissolved in CF$_3$COOH (6.5 ml) and stirred at room temperature for 40 mins. Cold ether (20 ml) was added to produce a precipitate, which was filtered and washed with ether (5×10 ml). The product was dried in vacuo over sodium hydroxide pellets. This material (318.5 mg) was dissolved in DMF (0.8 ml), to which was added N-methylmorpholine (10 l). The resulting solution had a pH of 7-8, measured with moist pH paper. After this neutralized solution was stirred at room temperature for 30 mins, a solution of p-nitrophenyl β-(S-benzylmercapto)-β,β-cyclopentamethylenepropionate, Nestor et al., *J. Med. Chem.*, vol. 18 (1975) at 284, (445 mg, 1.155 mmol in 0.4 ml of DMF) was added. The reaction mixture was stirred at room temperature. After 72 hours' stirring, TLC analysis using system D showed that the reaction mixture still contained a trace of the free octapeptide amide. N-Hydroxybenzotriazole monohydrate, Konig et al., *Chem. Ber.*, vol. 103 (1970) at 788, (39.3 mg, 0.26 mmol) was added. Coupling was complete within 5 hours. The precipitate was filtered, washed with cold ethyl acetate (4×10 ml) and dried in vacuo. The crude product (339 mg) was twice reprecipitated from DMF-methanol to give the acylpeptide amide (295.2 mg, 77.3%): mp 209°–211° C., $[\alpha]_D^{24} = -43.6°$ (c 0.5, DMF); R$_f$(E) 0.45, R$_f$(F) 0.63 Anal. (C$_{73}$H$_{94}$O$_{14}$N$_{14}$S$_3$) C, H, N.

(b) Total Synthesis on Resin

Boc-Tyr(Me)-Phe-Gln-Asn-Cys(Bzl)-Pro-Arg(Tos)-Gly-resin (1.11 g, 0.4 mmol prepared from Boc-Gly-resin using solid phase methodology) was converted to the acylotapeptide resin (1.167 g, weight gain 57 mg, 97.6% of theory) in one cycle of deprotection, neutralization and coupling with p-nitrophenyl β-(S-benzylmercapto)-β,β-cyclopentamethylenepropionate, see Nestor, supra. The resin was ammonolyzed, Manning, *J. Am. Chem. Soc.*, vol. 90 (1968) at 1348. The product was extracted with DMF. After the solvent was evaporated in vacuo, the residue was precipitated by addition of water. The crude product (410 mg) was twice reprecipitated from DMF-ethanol to give the acyloctapeptide (302 mg, 50.7% based upon initial glycine content of the resin); mp 206°–208° C. (decomp); R$_f$(E) 0.45; R$_f$(F) 0.63; $[\alpha]_D^{24} = -43.1°$ (c 1, DMF). Anal. (C$_{73}$H$_{94}$N$_{14}$O$_{14}$S$_3$) C, H, N.

Amino acid analysis: Tyr, 0.79; Phe, 1.01; Glu, 1.03; Asp, 1.04; Cys(Bzl), 0.97; Pro, 1.03; Arg, 0.99; Gly, 1.00; NH$_3$, 2.95.

EXAMPLE 2

β-(S-Benzylmercapto)-β,β-cyclopentamethylenepropionyl-Tyr(Bzl)-Phe-Gln-Asn-Cys(Bzl)-Pro-Arg(Tos)-Gly-HN$_2$ Boc-Tyr(Bzl)-Phe-Gln-Asn-Cys(Bzl)-Pro-Arg(Tos)-Gly-resin (1.46 g, 0.5 mmol) was converted to the acyloctapeptide resin (1.55 g, weight gain 70 mg, 95.9% of theory) as in Example 1 by one cycle of deprotection, neutralization and coupling with p-nitrophenyl β-(S-benzylmercapto)-β,β-cyclopentamethylenepropionate. The product obtained by ammonolysis of the resin was extracted with DMF. The solvent was evaporated in vacuo and the residue was precipitated by addition of water. The crude product (723 mg) was reprecipitated from DMF-ethanol and DMF-2% aqueous AcOH. Yield: 488 mg (62.4% based on initial Gly content on the resin); mp. 183°–185° C.; R$_f$(E) 0.38; R$_f$(D) 0.41; $[\alpha]_D^{23} = -23.9°$ (c 1, DMF). Anal. (C$_{79}$H$_{98}$N$_{14}$O$_{14}$S$_3$) C, H, N.

Amino acid analysis: Tyr, 0.97; Phe, 1.02; Glu, 1.05; Asp, 1.01; Cys(Bzl), 0.98; Pro, 1.04; Arg, 0.98; Gly, 1.00; NH$_3$.

EXAMPLE 3

[1-(β-Mercapto-β,β-cyclopentamethylenepropionic acid), 2-(O-methyl)tyrosine]arginine vasopressin

(a) From Nonapeptide Amide

A solution of the protected nonapeptide amide, prepared as in Example 1, (170 mg, 0.114 mmol) in 400 ml of ammonia (dried over sodium and redistilled) was stirred at the boiling point with sodium from a stick of the metal, contained in a small bore glass tube until a light blue color persisted in the solution for 30 sec, in accordance with du Vigneaud, *J. Am. Chem. Soc.*, vol. 76 (1954) at 3115. Dry glacial acetic acid (0.4 ml) was added to discharge the color. The solution was evaporated. A solution of the residue in aqueous acetic acid (0.2%, 800 ml), was treated with 2M ammonium hydroxide solution to give a solution of pH 7.5. To this stirred solution was added gradually an excess of a solution of potassium ferricyanide (0.01M, 11.4 ml), Hope et al., *J. Biol. Chem.*, vol. 237 (1962) at 1563. The yellow solution was stirred for 90 min more and for 1 h with anion-exchange resin (BioRad AG-3, Cl$^-$ form, 10 g damp weight). The suspension was filtered slowly through a bed of resin (80 g damp weight). The resin bed was washed with 300 ml of aqueous acetic acid and the combined filtrate and washings were lyophilized. The resulting powder (1386 mg) was desalted on a Sephadex G-15 column (110×2.7 cm) and eluted with aqueous acetic acid (50%) at a flow rate of 4 ml/h by the technique of Manning et al., *J. Chromatog.*, vol. 38 (1968) at 396. The eluate was fractionated and monitored for absorbance at 280 nm. The fractions comprising the major peak were pooled and lyophilized. The residue (55.5 mg) was further subjected to gel filtration on a Sephadex G-15 column (100×1.5 cm) and eluted with aqueous acetic acid (0.2M) at a flow rate of 2.5 ml/h. The peptide was eluted in a single peak (absorbance 280 nm). Lyophilization of the pertinent fractions yielded the vasopressin analog (49 mg, 37.3%); R$_f$(E) 0.19; R$_f$(F) 0.30; $[\alpha]_D^{22} = -59.6°$ (c 0.19, 1M AcOH).

Amino acid analysis: Tyr 0.81; Phe, 1.01; Glu, 1.04; Asp, 0.98; Pro, 1.04; Arg, 0.95; Gly, 1.00; NH$_3$ 3.10. Analysis following performic acid oxidation prior to hydrolysis according to Moore, *J. Biol. Chem.*, vol. 238 (1963) at 235, gave a Cys-(O$_3$H)-Gly ratio of 1.03:1.00.

(b) From Acyloctapeptide

Treatment of the acyloctapeptide (160 mg, 0.107 mmol) as described in Example 3(a) yielded the analog (64 mg, 51.7%), which was indistinguishable from the foregoing preparation by TLC: $[\alpha]_D^{23} = -59.1°$ (c 0.5, 1M AcOH).

Amino acid analysis: Tyr, 0.80; Phe, 1.02; Glu, 1.02; Asp, 0.98; Pro, 1.03; Arg, 0.96; Gly, 1.00; NH$_3$, 3.05. Analysis following performic acid oxidation prior to hydrolysis gave a Cys-(O$_3$H)-Gly ratio of 1.02:1.00.

EXAMPLE 4

[1-($\beta$-Mercapto-$\beta$,$\beta$-cyclopentamethylenepropionic acid), 2-substituted, 4-substituted, 9-desglycine]-arginine vasopressin The compounds were made in the same manner as the compounds of Examples 1-3, starting from Boc-Arg(Tos) resin, except that one fewer cycle of deprotection, neutralization and coupling was employed. Protected intermediates for each analog were obtained. Coupling with $\beta$-(S-benzylmercapto)-$\beta$,$\beta$-cyclopentamethylenepropionate was done in accordance with Nestor, supra.

Each precursor was deblocked with sodium in liquid ammonia to produce a sulfhydryl compound. The latter compounds were oxidatively cyclized with potassium ferricyanide, as in the preceding Examples. The analogs were desalted and purified by gel filtration on Sephadex G-15 by a two-step procedure using 50% acetic acid and 0.2M acetic acid, respectively, as eluants. The purity and identity of each analog was ascertained by thin-layer chromatography in three different solvent systems, BAW I (butan-1-ol-acetic acid, water 4:1:1 v/v), BAWP (butan-1-ol-acetic acid-water-pyridine 15:3:3:10 v/v) and BAW II (butan-1-ol-acetic acid-water 4:1:5 v/v, upper phase) with the following results:

| | R$_f$ | | |
|---|---|---|---|
| Compound | (BAW I) | (BAWP) | (BAW II) |
| desGly$^9$AVP | 0.04 | 0.27 | 0.23 |
| desGly$^9$d(CH$_2$)$_5$[D-Phe$^2$]VAVP | 0.39 | 0.59 | 0.39 |
| desGly$^9$d(CH$_2$)$_5$[D-Phe$^2$, Ile$^4$]AVP | 0.41 | 0.63 | 0.40 |
| desGly$^9$d(CH$_2$)$_5$[D-Tyr(Et)$^2$]VAVP | 0.39 | 0.60 | 0.38 |
| desGly$^9$d(CH$_2$)$_5$[Tyr(Et)$^2$]VAVP | 0.41 | 0.65 | 0.41 |

EXAMPLE 5

[1-($\beta$-Mercapto-$\beta$,$\beta$-cyclopentamethylenepropionic acid), 9-desglycinamide]arginine vasopressin This compound, desGly(NH$_2$)$^9$d(CH$_2$)$_5$AVP, was obtained from the protected precursor, $\beta$-(S-benzylmercapto)-$\beta$,$\beta$-cyclopentamethylenepropionyl-Tyr(Bzl)-Phe-Gln-Asn-Cys(Bzl)Pro-Arg(Tos)Bzl, which was synthesized in solution by the stepwise procedure of Bodansky et al., *J. Am. Chem. Soc.*, vol. 81 (1959) at 1173, starting from Boc-Arg(Tos)Bzl. Following cleavage of the Boc group with 1N HCl/HOAc and neutralization with triethylamine, successive couplings with Boc-Pro and Boc-Cys(Bzl) were performed, in the presence of dicyclohexylcarbodiimide (DCC) and hydroxybenzotriazole (HOBT) in accordance with Sheehan et al., *J. Am. Chem. Soc.*, vol. 77 (1955) at 1067 and Konig et al., *Chem. Ber.*, vol. 103 (1970) at 788.

The Asn and Gln residues were incorporated as corresponding Boc nitrophenyl esters. 1-Cyclohexyl-3-[2-morpholinyl-(5)-carbodiimide] (CMCD) and HOBT were used for coupling of Boc-Phe and Boc-Tyr(Bzl) to give the protected heptapeptide benzyl ester. Coupling with p-nitrophenyl $\beta$-(S-benzylmercapto)-$\beta$,$\beta$-cyclopentamethylene propionate, by the procedure of Nestor et al., supra, yielded the required protected intermediate. Deblocking with sodium in liquid ammonia and purification were carried out as above.

Purity of the compound was determined as above, with the following R$_f$ values:
BAW I: 0.07
BAWP: 0.18
BAW II: 023

EXAMPLE 6

[1-($\beta$-Mercapto-$\beta$,$\beta$-cyclopentamethylenepropionic acid), 2-D-phenylalanine, 4-valine, 9-desglycineamide]-arginine vasopressin The compound, desGly(NH$_2$)$^9$d(CH$_2$)$_5$[D-Phe$^2$]-VAVP, was obtained from the protected precursor, $\beta$-S-(benzylmercapto)-$\beta$,$\beta$-cyclopentamethylenepropionyl-D-Phe-Phe-Val-Asn-Cys(Bzl)-Pro-Arg(Tos)Bzl, which was synthesized in solution, starting from Boc-Phe-Val-Asn-Cys(Bzl)-Pro-Arg(Tos)-Bzl, prepared by custom synthesis by Alpha Biomedicals, Inc., San Carlos, Calif., except that cleavage of the Boc groups was done by trifluoroacetic acid, Boc-D-Phe was used instead of Boc-Tyr(Bzl) and coupling of $\beta$-(S-benzylmercapto)-$\beta$,$\beta$-cyclopentamethylenepropionic acid was mediated by DCC and HOBT to give the required protected intermediate.

The product was characterized by TLC with the following R$_f$ values:
BAW I: 0.40
BAWP: 0.46
BAW II: 0.39

EXAMPLE 7

[1-($\beta$-Mercapto-$\beta$,$\beta$-cyclopentamethylenepropionic acid), 2-D-phenylalanine, 4-isoleucine, 9-desamido]-arginine vasopressin A compound of the formula d(CH$_2$)$_5$[D-Phe$^2$, Ile$^4$]AVP acid was obtained from a protected precursor, $\beta$-S-(benzylmercapto)-$\beta$,$\beta$-cyclopentamethylenepropionyl-D-Phe-Phe-Ile-Asn-Cys(Bzl)-Pro-Arg(Tos)-Gly, which was synthesized by the solid phase method, starting from Boc-resin as in the foregoing examples, except that the partially protected precursor was cleaved from the resin by acidolysis with hydrogen bromide in trifluoroacetic acid containing anisole by the method of Walter et al., *J. Med. Chem.*, vol. 19 (1976) at 376. After evaporation of the trifluoroacetic acid, the product was obtained by precipitation from an acetic acid solution with diethyl ether. The intermediate was deblocked with sodium in liquid ammonia, reoxidized, lyophilized and purified as in the foregoing examples. The product was characterized by TLC, with the following values:
BAW I: 0.15
BAWP: 0.39
BAW II: 0.29

EXAMPLE 8

Antagonism to the vasopressor response was estimated in accordance with Dyckes et al., *J. Med. Chem.*, vol. 17 (1974) at 969. The values are expressed as pA$_2$ values, defined as in Schild et al., *Br. J. Pharmacol.*, vol. 2 (1947) at 189.

Activity as antidiuretic agonists was determined by intravenous injection of the compounds being evaluated in ethanol-anesthesized water-loaded rats in accordance with Sawyer, *Endocrinology*, vol. 63 (1958) at 694. Antagonism of the antidiuretic response to subsequent injections of arginine vasopressin was tested by the method of Sawyer et al., Science, vol. 212 (1981) at 49.

Antagonistic potencies were determined and expressed as "effective doses" and $pA_2$ values. The "effective dose" is defined as the dose (in nanomoles per kilogram) that reduces the response seen from 2x units of agonist injected 20 min after the dose of antagonist to the response with 1x units of agonist. Estimated in vivo "$pA_2$" values represent the negative logarithms of the effective doses, divided by the estimated volume of distribution (67 ml/kg). Results are given in Table 1.

| Q | Effective dose (nmoles/kg) | |
|---|---|---|
| | Anti-ADH | AntiVP |
| Arg(NH$_2$) | 0.67 ± 0.15 | 0.55 ± 0.09 |
| Ser(NH$_2$) | 0.55 ± 0.09 | 0.54 ± 0.09 |
| NH$_2$ | 0.66 ± 0.17 | 0.96 ± 0.09 |
| Ala(NH$_2$) | 0.31 ± 0.07 | 4.8 ± 1.2 |
| D-Ala(NH$_2$) | 2.9 ± 0.4 | 1.93 ± 0.23 |

These results show that the indicated modifications at the 9-position produce compounds which antagonize the antidiuretic action of AVP.

TABLE 1

| Compound | Agonistic Activities units/mg | | Anti-ADH | | Anti-VP | |
|---|---|---|---|---|---|---|
| | ADH | VP | ED | pA$_2$ | ED | pA$_2$ |
| AVP | 330 ± 23 | 382 ± 5 | — | — | — | — |
| AVP-acid[a,b] | 4.7 ± 0.6 | 0.03 | — | — | — | — |
| desGly$^9$AVP | 164 ± 4 | 0.05$^+$ | — | — | 68 ± 16 | 6.09 ± 0.10 |
| desGly$^9$(NH$_2$)AVP[c] | 5.6 ± 1.1 | 0.02$^+$ | — | — | — | — |
| d(CH$_2$)$_5$AVP | 0.03 ± 0.01 | — | — | — | 0.56 ± 0.11 | 8.16 ± 0.09 |
| desGly$^9$-d(CH$_2$)$_5$AVP | 0.003$^+$ | — | — | — | 0.27 ± 0.04 | 8.40 ± 0.06 |
| desGly(NH$_2$)$^9$—d(CH$_2$)$_5$AVP | 0.04 ± 0.01 | — | — | — | 0.73 ± 0.07 | 7.88 ± 0.06 |
| d(CH$_2$)$_5$[D-Phe$^2$]VAVP | weak$^+$ | — | 0.67 ± 0.13 | 8.06 ± 0.09 | 0.58 ± 0.04 | 8.06 ± 0.03 |
| desGly$^9$-d(CH$_2$)$_5$[D-Phe$^2$]VAVP | — | — | 0.58 ± 0.11 | 8.09 ± 0.08 | 0.47 ± 0.04 | 8.15 ± 0.03 |
| desGly(NH$_2$)$^9$—d(CH$_2$)$_5$—[D-Phe$^2$]VAVP | — | — | 1.30 ± 0.35 | 7.75 ± 0.11(4) | 0.80 ± 0.08 | 7.93 ± 0.05(4) |
| d(CH$_2$)$_5$[Tyr(Et)]$^2$VAVP | 0.03$^+$ | — | 1.9 ± 0.2 | 7.57 ± 0.06 | 0.49 ± 0.11 | 8.16 ± 0.09 |
| desGly-d(CH$_2$)$_5$[Tyr(Et)$^2$]VAVP | — | — | 1.0 ± 0.2 | 7.89 ± 0.09 | 0.45 ± 0.02 | 8.18 ± 0.02 |
| d(CH$_2$)$_5$[D-Tyr(Et)$^2$]VAVP | weak$^+$ | — | 1.1 ± 0.2 | 7.81 ± 0.07 | 0.45 ± 0.11 | 8.22 ± 0.12 |
| desGly-d(CH$_2$)$_5$[D-Tyr(Et)$^2$]VAVP | — | — | 1.8 ± 0.3 | 7.58 ± 0.07 | 0.45 ± 0.04 | 8.17 + 0.04 |
| d(CH$_2$)$_5$[D-Phe$^2$, Ile$^4$]AVP | — | — | 0.46 ± 0.07 | 8.24 ± 0.08 | 0.99 ± 0.12 | 7.86 ± 0.05 |
| desGly$^9$-(CH$_2$)$_5$-[D-Phe$^2$, Ile$^4$]AVP | — | — | 0.66 ± 0.17 | 8.05 ± 0.09 | 1.0 ± 0.1 | 7.84 ± 0.03 |
| d(CH$_2$)$_5$[D-Phe$^2$, Ile$^4$]AVP acid | — | — | 6.42 ± 2.06 | 7.11 ± 0.11 | 7.95 ± 1.28 | 6.94 ± 0.08 |

[a]AVP-acid was purchased from Bachem, Inc.
[b]This compound was originally reported as being an ADH antagonist in vitro and in vivo, Dousa et al., supra. These results show it is an antidiuretic agonist in vivo.
[c]Originally obtained by tryptic cleavage of AVP, du Vigneaud et al., J. Am. Chem. Soc., vol. 75 (1953) at 4880.
$^+$Compounds showed weak partial agonistic activities in these assays, in a way not clearly related to dose.

EXAMPLE 9

[1-($\beta$-Mercapto-$\beta,\beta$-cyclopentamethylenepropionic acid), 2-D-phenylalanine, 4-isoleucine, 9-substituted]-arginine vasopressin (a) Synthesis Compounds of this series were prepared as in the foregoing examples, except that an amino acid, other than glycine, was attached to the resin in the first cycle of the synthesis. The compounds obtained were of the formula d(CH$_2$)$_5$[D-Phe$^2$, Ile$^4$, Q$^9$]AVP and were characterized by TLC as in the foregoing examples. The following results were obtained:

| Q | R$_f$ | | |
|---|---|---|---|
| | (BAW I) | (BAWP) | (BAW II) |
| Arg(NH$_2$) | 0.11 | 0.37 | 0.27 |
| Ser(NH$_2$) | 0.39 | 0.59 | 0.35 |
| Ala(NH$_2$) | 0.41 | 0.64 | 0.37 |
| D-Ala(NH$_2$) | 0.42 | 0.64 | 0.37 |
| NH$_2$ | 0.45 | 0.64 | 0.41 |

(b) Evaluation

The compounds were evaluated as in Example 6 to determine effective doses as antagonists of the antidiuretic action of arginine vasopressin. The following results were obtained:

The preceding examples can be repeated with similar success by substituting the generically or specifically described reactants and/or operating conditions of this invention for those used in the preceding Examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A compound of the formula

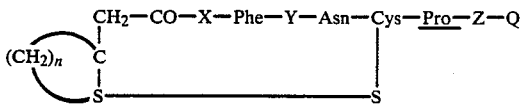

wherein n is 4 or 5; X is (D- or L-)Tyr(R), D-Phe, D-Val, D-Leu, D-Ile, D-Nva, D-Nle, D-Cha, D-Abu, D-Thr, D-Asn, D-Gln or D-Met; Y is Val, Ile, Thr, Ala, Lys, Cha, Nva, Met, Nle, Orn, Ser, Asn, Gln, Phe, Tyr, Gly, Abu or Leu; Z is (D- or L-)Arg, Orn or Lys; Q is Arg(NH$_2$), Ser(NH$_2$), (D- or L-)Ala(NH$_2$), Gly, OH or NH$_2$ and R is methyl, ethyl, propyl or butyl, provided that when Y is Val or Gln, R is also H.

2. A compound of claim 1, wherein X is D-Phe.

3. A compound of claim 1, wherein X is D-Tyr(R) and R is methyl, ethyl, propyl or butyl.

4. A compound of claim 1, wherein Y is Val.

5. A compound of claim 1, wherein Y is Ile.
6. A compound of claim 1, wherein Z is Arg.
7. A compound of claim 1, wherein Q is NH₂.
8. A compound of claim 1, wherein Q is Arg(NH₂).
9. A compound of claim 1, wherein Q is Ser(NH₂).
10. A compound of claim 1, wherein Q is (D- or L-)Ala(NH₂).
11. A compound of claim 1, wherein Q is OH.
12. A compound of claim 1, wherein n is 5.
13. [1-(β-Mercapto-β,β-cyclopentamethylenepropionic acid), 2-D-phenylalanine, 4-valine, 9-desglycine]-arginine vasopressin, a compound of claim 1.
14. [1-(β-Mercapto-β,β-cyclopentamethylenepropionic acid), 2-D-phenylalanine, 4-isoleucine, 9-desglycine]-arginine vasopressin, a compound of claim 1.
15. [1-(β-Mercapto-β,β-cyclopentamethylenepropionic acid), 2-D-(O-ethyl)tyrosine, 4-valine, 9-desglycine]-arginine vasopressin, a compound of claim 1.
16. [1-(β-Mercapto-β,β-cyclopentamethylenepropionic acid), 2-D-phenyl-alanine, 4-isoleucine, 9-argininamide]-arginine vasopressin, a compound of claim 1.
17. [1-β-Mercapto-β,β-cyclopentamethylenepropionic acid), 2-D-phenyl-alanine, 4-isoleucine, 9-serinamide]-arginine vasopressin, a compound of claim 1.
18. [1-β-Mercapto-β,β-cyclopentamethylenepropionic acid), 2-D-phenyl-alanine, 4-isoleucine, 9-alanamide]-arginine vasopressin, a compound of claim 1.
19. [1-(β-Mercapto-β,β-cyclopentamethylenepropionic acid), 2-D-phenylalanine, 4-valine, 9-desglycinamide]-arginine vasopressin, a compound of claim 1.
20. A method for antagonizing the in vivo response of an animal to the antidiuretic and/or vasopressor action of an antidiuretic hormone, comprising administering to the animal being treated an amount of a compound of claim 1, in admixture with a physiologically and pharmaceutically acceptable carrier, effective to antagonize the antidiuretic and/or vasopressor responses to the antidiuretic hormone.
21. A method for antagonizing the in vivo response of an animal to the antidiuretic action of an antidiuretic hormone, comprising administering to the animal being treated an amount of a compound of claim 14, in admixture with a physiologically and pharmaceutically acceptable carrier, effective to antagonize the antidiuretic response to the antidiuretic hormone.
22. A method for antagonizing the in vivo response of an animal to the antidiuretic action of an antidiuretic hormone, comprising administering to the animal being treated an amount of a compound of claim 18, in accordance with a physiologically and pharmaceutically acceptable carrier, effective to antagonize the antidiuretic response to the antidiuretic hormone.
23. A compound of claim 1, wherein X is (D- or L-)Tyr(R), Y is Val or Gln and R is H, methyl, ethyl, propyl or butyl.
24. A compound of claim 23, wherein Z is Arg.

25. A method of antagonizing the in vivo response of an animal to the vasopressor action of a vasopressor hormone, comprising administering to the animal being treated an amount of a compound of claim 23, in admixture with a physiologically and pharmaceutically acceptable carrier, effective to antagonize the vasopressor response to the hormone.

26. A compound of the formula

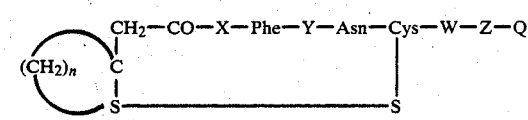

wherein n is 4 or 5; W is Pro or dehydro-Pro; X is (D- or L-)Tyr(R), D-Phe, D-Val, D-Leu, D-Ile, D-Nva, D-Nle, D-Cha, D-Abu, D-Thr, D-Asn, D-Gln, D-Met, or D-Pba; Y is Val, Ile, Thr, Ala, Lys, Cha, Nva, Met, Nle, Orn, Ser, Asn, Gln, Phe, Tyr, Gly, Abu or Leu; Z is (D- or L-)Arg, Orn or Lys; Q is Arg(NH₂), Ser(NH₂), (D- or L-)Ala(NH₂), Gly, OH, NH₂, NH(R) or NHBzl and R is methyl, ethyl, propyl or butyl, provided that when Y is Val or Gln, R is also H.

27. A compound of the formula

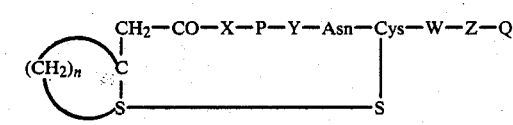

wherein n is 4, 5, or 6; P is Phe or Phe(4′alk); W is Pro or dehydro-Pro; X is (D- or L-)Tyr(R), D-Phe, D-Val, D-Leu, D-Ile, D-Nva, D-Nle, D-Cha, D-Abu, D-Thr, D-Asn, D-Gln, D-Met, D-Pba, D-Chg or D-alle; Y is Val, Ile, Thr, Ala, Lys, Cha, Nva, Met, Nle, Orn, Ser, Asn, Gln, Phe, Tyr, Gly, Abu Leu or D-Chg; Z is (D- or L-)Arg, Orn or Lys; Q is Arg(NH₂), Ser(NH₂), (D- or L-)Ala(NH₂), Gly, OH, NH₂, NH(R) or NHBzl and R is methyl, ethyl, propyl or butyl, provided that when Y is Val or Gln, R is also H.

28. A compound of formula

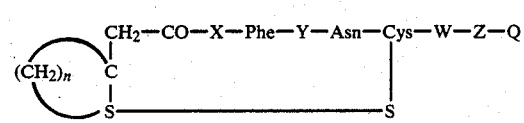

wherein
n is 4 or 5;
W is Pro or dehydro-Pro;
X is D-Tyr(R), D-Phe, D-Val, D-Leu, D-Ile, D-Nva, D-Nle; D-Cha, D-Abu, D-Thr, D-Asn, D-Gln, D-Met, or D-Pba;
Y is Val;
Z is (D- or L-)Arg, Orn or (D- or L-)Lys;
Q is OH, NH₂, NH(R) or NHBzl;
R is H or lower alkyl of 1 to 4 carbons, or a pharmaceutically acceptable salt thereof.

* * * * *